United States Patent [19]

Nicolson et al.

[11] Patent Number: 5,306,352
[45] Date of Patent: Apr. 26, 1994

[54] PEROXIDE DISINFECTION METHOD

[75] Inventors: Paul Nicolson, Dunwoody; Kenneth R. Seamons, Marietta; Fu-Pao Tsao; Larry A. Alvord, both of Lawrenceville; Earl C. McCraw, Deluth, all of Ga.

[73] Assignee: Ciba-Geigy Corporation, Ardsley, N.Y.

[21] Appl. No.: 7,809

[22] Filed: Jan. 22, 1993

Related U.S. Application Data

[63] Continuation of Ser. No. 636,280, Dec. 31, 1990, abandoned, which is a continuation-in-part of Ser. No. 458,123, Dec. 28, 1989, Pat. No. 5,078,798.

[51] Int. Cl.$^5$ .......................... B08B 3/08; B08B 7/00
[52] U.S. Cl. ...................................................... 134/42
[58] Field of Search ............................................ 134/42

[56] References Cited

U.S. PATENT DOCUMENTS

3,912,451 10/1975 Gaglia, Jr. ............................ 134/42

FOREIGN PATENT DOCUMENTS

| | | |
|---|---|---|
| 32246/84 | 2/1985 | Australia . |
| 32247 | 2/1985 | Australia . |
| 56627/86 | 10/1986 | Australia . |
| 60652/86 | 3/1987 | Australia . |
| 64243/86 | 5/1987 | Australia . |
| 61664/86 | 8/1987 | Australia . |
| 79703 | 4/1988 | Australia . |
| 147100 | 9/1989 | European Pat. Off. . |
| 0354876 | 2/1990 | European Pat. Off. . |
| 0436466 | 7/1991 | European Pat. Off. . |

Primary Examiner—R. Bruce Breneman
Assistant Examiner—Zeinab El-Arini
Attorney, Agent, or Firm—Wenderoth, Lind & Ponack

[57] ABSTRACT

A method of disinfecting a hydrogen peroxide stable material by contacting said material with a hydrogen peroxide containing solution and a hydrogen peroxide decomposition means adapted to permit said material to have a cumulative (% peroxide)·(min) exposure from the time said decomposition means contacts said hydrogen peroxide containing solution over a period not exceeding 12 hours of at least 20% (peroxide)·(min). Also, disclosed are devices and components thereof whereby said method can be achieved.

34 Claims, 14 Drawing Sheets

PEROXIDE DISINFECTION METHOD

This application is a continuation of application Ser. No. 07/636,260, filed Dec. 31, 1990, now abandoned, which in turn is a continuation-in-part of application Ser. No. 07/458,123, filed Dec. 28, 1989, entitled Buoyancy Mediated Control of Catalytic Reaction, now U.S. Pat. No. 5,078,798.

FIELD OF THE INVENTION

The invention relates to hydrogen peroxide disinfection methods and devices. It is especially relevant to those methods and devices particularly adapted to the $H_2O_2$ disinfection of contact lenses, most especially soft contact lenses.

BACKGROUND OF THE INVENTION

In the area of peroxide disinfection of surfaces, residual peroxide must be removed from the disinfected surface due to sensitivity of other materials with which the disinfected surface comes in contact. This is especially so in the contact lens disinfection area where the disinfected lens will be placed directly on the eye. In the past, this has been accomplished by methods such as dilution with large volumes of water or saline or exposing the solution and/or disinfected material to a hydrogen peroxide decomposing agent or catalyst for a time sufficient to reduce the residual hydrogen peroxide to acceptable levels. Unfortunately, in many settings, especially in the contact lens field, dilution is not a commercially viable or user practical alternative. Furthermore, where the decomposition agent or catalyst is used, the regimen becomes bothersome in the number of steps involved and the degree of user involvement necessary. As the complexity of the regimen goes up, strict compliance with that regimen drops off dramatically. Hence, more user friendly single step processes have been attempted. Most notable and relevant to the instant invention in current use in the AO Sept system. This system operates by placing a contact lens to be disinfected in contact with a solution of peroxide and a platinum disk whereby peroxide disinfection and decomposition occur essentially simultaneously. The only user input is to place the components in the system and wait the appropriate time interval before removing the lenses.

Unfortunately, many times users do not follow the regimen sufficiently so that there is the risk that complete disinfection has not occurred or decomposition has not sufficiently taken place.

In a typical hydrogen peroxide system in which the hydrogen peroxide is contacted with hydrogen peroxide with the simultaneous introduction of contact lenses for disinfection, the hydrogen peroxide depletes rapidly and the disinfection at the higher concentrations is short. For example, in an AO Sept system in which the initial concentration of hydrogen peroxide is 3%, the concentration of the hydrogen peroxide falls rapidly to about 0.1% in about 12.5 minutes. After this point, the concentration decreases very slowly and it takes several hours, i.e. up to 8 hours or more, before the hydrogen peroxide is depleted sufficiently to ocularly safe or acceptable levels whereby the contact lens can be inserted into the eyes without fear of irritation or injury.

In some instances, it is desirable, however, to control the catalytic reaction of the hydrogen peroxide such that concentration of the hydrogen peroxide is high over a longer transition period and ideally to control the system so that the hydrogen peroxide concentration can be maintained at high levels for a longer period of time and then abruptly reduced to ocularly acceptable levels. This longer transition time is especially important where the materials to be disinfected are heavily contaminated. There is, therefore, a need for an improved hydrogen peroxide disinfectant system which makes it possible to control the decomposition rate of the hydrogen peroxide.

OBJECTS OF THE INVENTION

It is an object of the present invention to provide an improved hydrogen peroxide disinfection regimen than those currently available.

It is another object of the invention to provide a simple single-step disinfection method for use with hydrogen peroxide.

It is still another object of the invention to provide a method of carrying out a catalytic reaction in a controlled manner which allows for greater transition times for the material to be disinfected in an $H_2O_2$ solution at higher $H_2O_2$ concentrations than in prior art hydrogen peroxide-catalyst systems.

SUMMARY OF THE INVENTION

The present invention relates to a method of disinfecting a hydrogen peroxide stable material by contacting said material with a hydrogen peroxide containing solution and a hydrogen peroxide decomposition means adapted to permit said material to have a longer exposure at higher concentrations than previously afforded by conventional peroxide disinfectant systems. This is achieved by utilizing a hydrogen peroxide decomposition means which permits the material to be disinfected such as to have a cumulative (% peroxide)·(min) exposure from the time the decomposition means contacts the hydrogen peroxide containing solution over a period not exceeding 12 hours of at least 20% peroxide·min. Also disclosed are devices and components whereby said method can be achieved.

DETAILED DESCRIPTION OF THE INVENTION

The cumulative exposure described in the present application is that exposure from the time the composition means, such as a catalyst, contacts the peroxide containing solution, i.e. time zero, over a period of no greater than 12 hours of at least 20% peroxide·min. This cumulative exposure is a convenient mathematical means of determining the rate of decomposition of the hydrogen peroxide in the hydrogen peroxide system. It is arrived at by plotting the percentages of hydrogen peroxide against time as in FIGS. 1 and 2, determining the area under the curve at various time intervals and plotting this cumulative area against the time.

Figure 1:
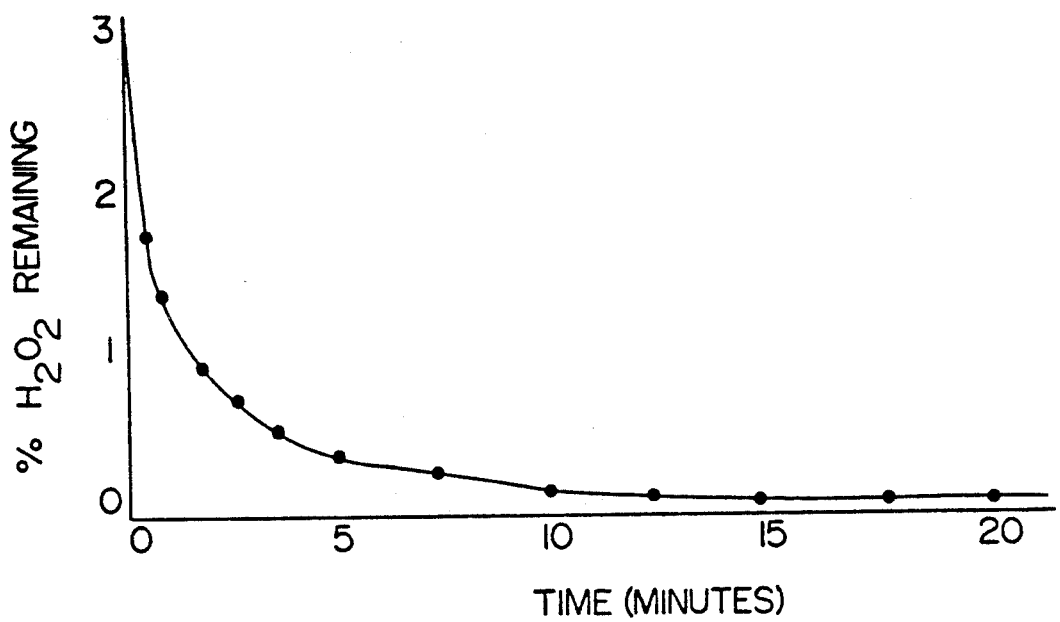
FIG. 1 is a prior art AO Sept system in which a platinum catalyst is plotted with a 3% hydrogen peroxide solution and the rate of decomposition of hydrogen peroxide plotted against time.

In FIG. 1 a typical prior art AO Sept system is depicted in which a platinum catalyst is contacted with a 3% hydrogen peroxide solution and the rate of decomposition plotted on the graph. In such situation, it will be noted that the concentration of $H_2O_2$ falls rapidly to about 0.1% in 12.5 minutes.

Figure 2:
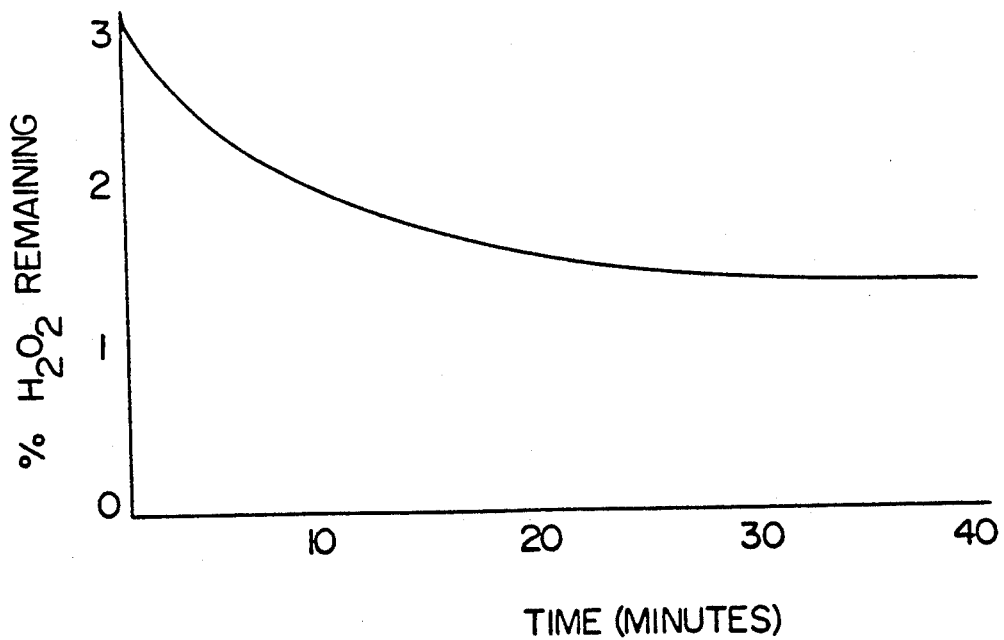
FIG. 2 represents a typical decomposition profile of a 3% $H_2O_2$ system controlled, according to the present invention, to decrease slowly over time.

FIG. 2, however, represents a typical decomposition profile of a hydrogen peroxide system in which the rate of decomposition of the hydrogen peroxide is controlled so that the concentration of hydrogen peroxide decreases more gradually over time.

To determine the cumulative area, the area under the curves in FIGS. 1 and 2, for example, are integrated or calculated at various time intervals to determine the cumulative area or the sum of the areas in terms of percent peroxide·min. These areas in turn are plotted against time to determine the rate at which the hydrogen peroxide decomposes with time. The cumulative exposure vs. time graph is thus an accurate way of mathematically expressing the disinfectant capacity of the system at any given time.

As previously point out, it is desirable to control the rate of decomposition so that a relatively higher concentration of hydrogen peroxide remains in the system over a longer transition time. As can be seen by FIG. 1, the area under the curve from 0 to some positive time interval, for example 5 minutes, is smaller than the area under the curve from 0 to 5 minutes in FIG. 2. Thus, the higher the cumulative area, the lower the decomposition rate of the hydrogen peroxide. In this connection, note that the cumulative area is expressed in % (peroxide) (minutes) because the ordinate of the curve is expressed in percentages and the abscissa in minutes. The calculated value of the area is, therefore, expressed in terms of % peroxide·min.

According to the present invention, the cumulative area or cumulative exposure is calculated from such graphs as FIGS. 1 and 2 above are then plotted against time to determine the cumulative exposure at various time intervals. Such a typical graph is shown in FIG. 3 of the drawings in which the effect of the catalyst rate (of decomposing the $H_2O_2$) is depicted therein.

Figure 3:
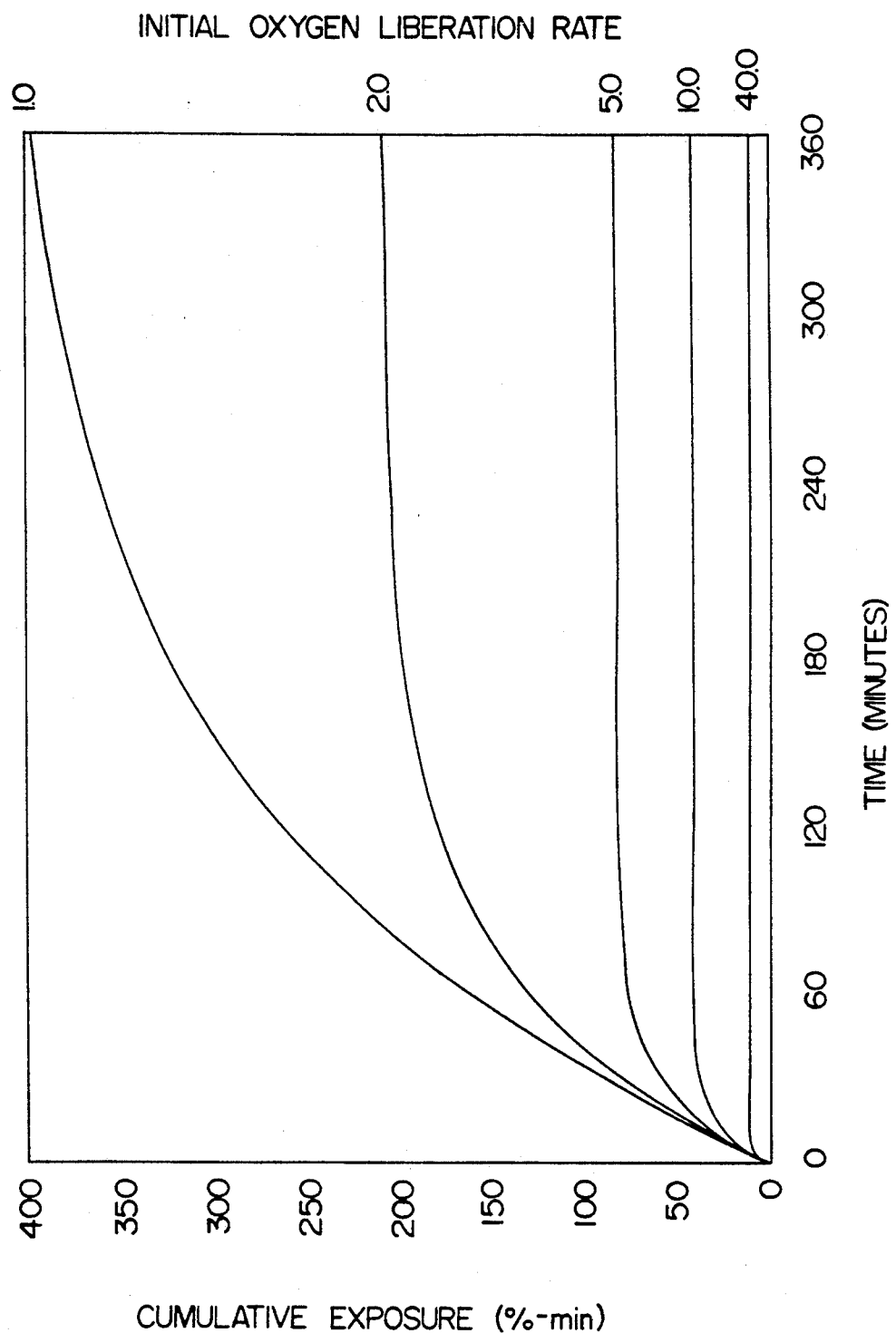
FIG. 3 represents various catalyst systems in which both the cummulative exposure in percent minutes and the initial oxygen liberation rate is plotted against time.

According to FIG. 3, the prior art AO Sept system with the platinum catalyst fixed at the bottom thereof (and which has not been modified to control the cumulative exposure as in the present invention) is a relatively straight line represented by line 1 in the graph in which the cumulative exposure is about 10. At the right hand side of the graph, there are depicted the initial oxygen liberation rates. It can be seen that for the conventional AO Sept system, a high liberation rate of oxygen of about 40 ml/min. is initially generated. The oxygen liberation rate, of course, is a means of determining the decomposition rate of the hydrogen peroxide, since the hydrogen peroxide is decomposed by means of the catalyst to produce water and nascent oxygen. The oxygen liberation rate is, therefore, a means of determining the rate of decomposition and the cumulative exposure of the material to be disinfected. It can be further seen from this graph that as the cumulative exposure rises above 20% min., the generation of the oxygen is greatly decreased to between about 15 ml/min. to about 1.0 ml/min., depending on the means adopted to control the cumulative exposure of the contact lens, etc. to be disinfected. This particular graph is designed to illustrate how the cumulative exposure is related to the decomposition rate of $H_2O_2$ in the system.

There are several practical means of controlling the disinfectant capacity of the hydrogen peroxide system such that the material to be disinfected has a cumulative exposure of at least 20% peroxide min. over a period of no greater than 12 hours. Before discussing such concrete means, a general description of the primary considerations which go into the catalytic decomposition of hydrogen peroxide will be discussed.

There are generally five important steps to consider in the catalytic decomposition of hydrogen peroxide, which steps can be broadly described as follows:

(1) the transportation of the $H_2O_2$ to the catalyst to insure a continuous contact between the catalyst and hydrogen peroxide.

(2) the absorption of hydrogen peroxide to the catalyst surface.

(3) the neutralization or catalysis in which the hydrogen peroxide is decomposed to water and nascent oxygen.

(4) the desorption from the surface of the reaction products, i.e. the water and nascent oxygen, or other contaminants so as to reexpose the active sites.

(5) the transportation of the reaction products away from the surface.

There are various concrete means to control the decomposition rate of the hydrogen peroxide by taking into consideration the factors which go into the catalytic decomposition as described above, such as to control the cumulative exposure of the material to be disinfected in the hydrogen peroxide solution.

One such means is to prepoison the catalyst before it is sold and subjected to the first use by the user. In a typical catalytic decomposition of hydrogen peroxide, the active sites of the catalyst are naturally deactivated to various degrees over a period of time by absorption or contamination of the surface with the reaction products, etc. Such deactivation, in turn, slows down the decomposition rate of the hydrogen peroxide whereby the cumulative area under the curve or cumulative exposure as described above is increased. In order to control the catalytic rate of decomposition, according to the present invention, a catalyst, such as platinum, is prepoisoned by, for example, subjecting it to a hydrogen decomposition catalytic reaction to partially deactivate the active sites prior to sale to the user of the catalyst-hydrogen peroxide decomposition device so that the cumulative exposure is controlled from the outset. To determine whether the catalyst is sufficiently prepoisoned, the generation of oxygen from the system can be measured. Thus, as previously described, in a typical AO Sept system using platinum as a catalyst, the initial generation of oxygen is 40 ml/min. See FIG. 3, right hand side of the drawings. To sufficiently prepoison the catalyst so that the cumulative exposure is over 20%·min., the oxygen liberated during the reaction is periodically measured until the oxygen liberation rate is somewhere between 15 ml/min. and preferably between about 2 and 5 ml/min to correlate with the minimum 20% minimal exposure shown on the graph.

Figure 4:
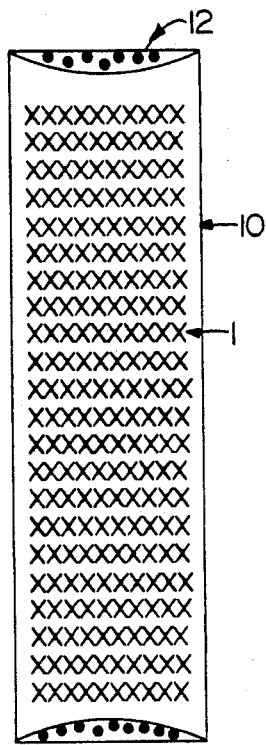
FIG. 4 represents a means of controlling the cumulative exposure by partially enclosing the catalyst in a container, such as a tube, with openings therein to control the escape of oxygen from the catalyst system during the catalytic reaction.

In another means of controlling the cumulative exposure, the catalyst 1 can be partially enclosed in a container 10 such as a tube with openings 12 in the tube to control the escape of oxygen from the system to approximately 2-15 and preferably 2-3 ml/min. As stated previously, this device can be a simple tube 10 containing small orifices 12 at the top or bottom calibrated to leak out the oxygen to an amount approximating 2-15 ml/min. and preferably 2-3 ml/min. Such a device is described in FIG. 4 of the drawings. The device can be further modified such that the sides of the tube 10 contain tiny perforations therein to permit the escape of the oxygen gas through said perforations. Although a tube is depicted therein, a container of any shape can be employed as long as it is calibrated to control the escape of oxygen from the catalyst.

Another convenient means of controlling the decomposition of the hydrogen peroxide and the cumulative area under the curve as described above is through a buoyancy mediated control catalytic reaction as described in the parent application Ser. No. 07/458,123, filed Dec. 28, 1989. This buoyancy mediated control system will be subsequently described in detail.

The catalyst used also is an important factor in controlling the decomposition rate. The activity of various catalysts differs considerably with such catalyst as Pt exhibiting a high decomposition rate per unit surface to Au which has decomposition rate which may be practically too low, for most $H_2O_2$ disinfectant systems. The order of $H_2O_2$ decomposition/unit surface area for various catalyst systems is as follows:

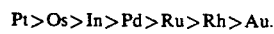

Pt>Os>In>Pd>Ru>Rh>Au.

The selection of the proper catalyst with any of the aforementioned means is therefore an important factor. Although any of such catalysts, among others conventionally employed, may be used to decompose $H_2O_2$, it is preferred to use a catalyst having a high rate of decomposition, such as Pt, and to modify it to slow down the reaction rate according to one of the procedures outlined above.

As a specific procedure of controlling the decomposition rate of the $H_2O_2$ and the cumulative exposure, the buoyancy mediated catalytic control embodiment of the present invention will be described in detail as a means of exemplifying the characteristic features of the present invention.

BUOYANCY MEDIATED CONTROL SYSTEM FOR INCREASING THE EXPOSURE TIME AT HIGHER CONCENTRATIONS

According to such buoyance mediated control system, the catalytic reaction is carried out in (a) a $H_2O_2$ liquid which generates a gas (oxygen) that gives the catalytic particle sufficient buoyancy to rise to the surface of the liquid phase or (b) a liquid wherein the reaction product solution is of a significantly different density than and substantially non-miscible with the reactant solution and the catalytic particle is of appropriate density that at least a portion thereof tends to remain in contact with the reactant solution portion and of sufficient buoyancy so as to be at or near the reactant solution/reaction product solution interface. The present invention is primarily interested in the first reaction (a).

Buoyancy controlled catalytic reactions fall into two primary types of reactions. First are those reactions which generate a gas. The gas bubbles adhere to the surface of the catalyst particle creating a buoyant particle. The buoyant particle rises to the surface where the gas bubble escapes to the gas phase over the liquid reaction medium. Upon losing the gas bubbles, the catalyst loses buoyance and begins to descent until it again contacts liquid containing reactants so that further buoyant gas bubbles can be generated. This bobbing action is, therefore, confined to the uppermost layers of the reactant solution and the reaction product solution, leaving the lower portion of the reactant solution substantially undisturbed for a significant portion of time.

Depending on the speed with which a particular reaction is intended to take place, the buoyancy of the catalyst can be altered by coating a carrier or substrate particle of particular density with varying amounts of catalyst. The less dense the particle, the more it will extend the reaction time as such as particle will be confined more to the uppermost reactant solution portions and reaction product solution. Similarly, the greater the amount of catalyst at the particle surface, the more the particle will find itself in the uppermost reactant solution and reaction product solution. Particle shape also plays a part in reaction rate control. Spherical particles will tend to lose their gas bubble lifters quicker than other shapes; yet they move more easily through the liquid solutions than other particle shapes. Finally, particle size is important in control of the reaction rate in relation to changes in particle weight vs. particle surface area. The greater the weight, the more buoyant force needed from gas bubbles; if surface area does not increase at least as rapidly, then the particle will reside for a greater time in the reactant solution area and thereby speed up the reaction more so than otherwise. Counterbalancing this is the fact that the greater the catalyst surface area, the faster the reaction, and the shorter the residence time of the article to be disinfected in the disinfectant.

In the second type of buoyancy controlled catalytic reaction, the catalytic particle resides, due to its density, at or near the reactant solution/reaction product solution interface, at least part of it tending to remain in contact with the reactant solution. If the reaction product solution is less dense than the reactant solution, then the reaction proceeds substantially from top to bottom and the catalytic particles are designed to be slightly less dense than the reactant solution (i.e. between the reaction product and reactant solution densities). If the reaction product solution is more dense than the reactant solution, then the reaction proceeds from bottom to top and the catalytic particle is designed to be slightly more dense than the reactant solution. In either event, the catalytic particle must return to contact reactant solution if the reaction is to continue to proceed. If the reaction product adheres to the catalyst for sufficient time to drive the catalyst toward the reaction product solution, the catalyst particles may also be of the same density as the reactant solution in either of the cases described.

Typical catalytic reactions of the first type include, but are not limited to, a hydrogen peroxide solution with peroxidase, catalase, or transition metals such as platinum, palladium, etc. and compounds thereof such as iron oxide, manganese oxide or $TiO_2$ catalyst particles. In fact, such catalyst systems can be employed in all of the decomposition means contemplated by the present invention.

Typical catalytic particles can be prepared from refractory, plastics, fiber, etc. particles having an appropriate configuration which are then overcoated or impregnated with a catalyst, such as platinum, catalase, etc.

Convenient particle shapes include but are not limited to discs, plates, spheres, starts, "donuts", wafers, tubes, rods and strips. Essentially any particle shape will suffice.

Suitable particle sizes for spheres are particles with diameters of from about 0.5 mm up to about 5 cm, preferably about 1 mm to about 2 cm, more preferably about 3 mm to about 1 cm, most preferably about 4 mm to about 8 mm. Suitable, although not limiting for a plate or disc, or wafer shape is 1 cm×2 cm×0.02 cm. Appropriate size limits for other shapes can readily be inferred by those of ordinary skill. To balance particle size and surface area to the desired ratio, one may use multiple smaller sized particles, for Example 3 particles of 1 mm diameter each instead of one particle of equivalent weight or surface area.

For the second embodiment of the buoyancy mediated control system, the catalyst particle does not vary far from the reactant solution/reaction product solution interface, and particle movement considerations are less important. Hence, there is greater flexibility in terms of catalyst shape and more concern with appropriate density for the particle. While it is expected that there is going to be little if any "bobbing" action, such movement is not precluded. In fact, to the extent the reaction product generated by the catalytic reaction adheres to the catalyst, there may be some significant positive or negative buoyant effect (depending upon whether the product solution is less dense or more dense than the reactant solution). Beyond these concerns, the catalytic particles for use in the first embodiment are also suitable for use in the second embodiment of the present invention.

The gas producing reaction contemplated herein represents the degeneration of hydrogen peroxide to water and oxygen gas. In such gas generating reactions, preferable particle shapes are stars, plates, discs, wafers, spheres, rods, strips and donuts; more preferably, spheres, donuts, rods, plates, discs and wafers; most preferably plates, discs, wafers and spheres.

The particular density of the catalytic particle is dependent upon how fast and far the particle is to penetrate back into the reactant solution phase. For a given shape, the greater the density, the longer it will take to generate sufficient buoyant force to lift it out of the reactant solution phase (in gas generating systems and those where reaction products are less dense than reactants), yet as the surface area increases relative to weight, the less time the particle will spend in the reactant solution.

For the hydrogen peroxide/oxygen gas system of this invention, the preferred parameters are such that the density of the catalyst particle is from 1.05 to about 1.30, preferably from about 1.10 to about 1.20, most preferably from about 1.12 to about 1.18; the surface area of the particle of about 0.008 to about 75 cm$^2$, preferably about 0.03 cm$^2$ to about 13 cm$^2$, more preferably about 0.2 cm$^2$ to about 5 cm$^2$, most preferably about 0.3 cm$^2$ to about 3.2 cm; and the surface area/weight ratio of the particle of from about 0.85 to about 116, preferably about 1.15 to about 54.5, most preferably about 2.95 to about 11.3.

The surface may be anything from smooth to rough with rough surfaces provided a larger effective surface area than the same sized and shaped particle of smooth morphology. The rough morphology will also allow for greater "lifter" adherence.

Figure 5:
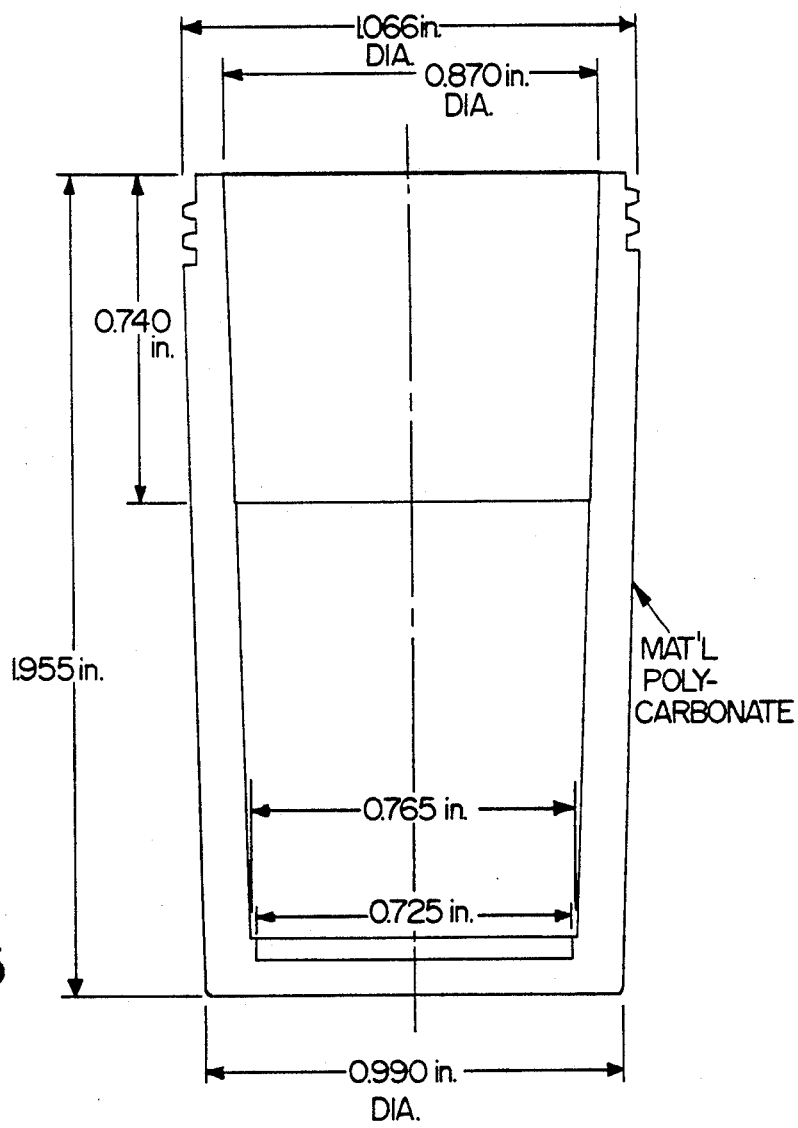
FIG. 5 is a sample cup used to measure the percentage of peroxide in the vicinity of a contact lens to be sterilized according to the method of the present invention.

The hydrogen peroxide/oxygen gas system has a decomposition profile, such that total area under the % peroxide (in the vicinity of the lens) vs. time is in excess of at least 20%·min, preferably 47% min, more preferably in excess of 50% min, even more preferably greater than about 75% min, still more preferably more than about 100% min, most preferably in excess of about 120% min, and ideally more than about 140% min, when using a current commercially available AO Sept cup, approximately 3% peroxide, and sampling the peroxide in the vicinity of the lens with the lens placed standing on edge at the bottom of the cup and the cup filled to the indicated line. A sample cup used in these tests for conformity with the decomposition profile is shown in FIG. 5.

Figure 6:
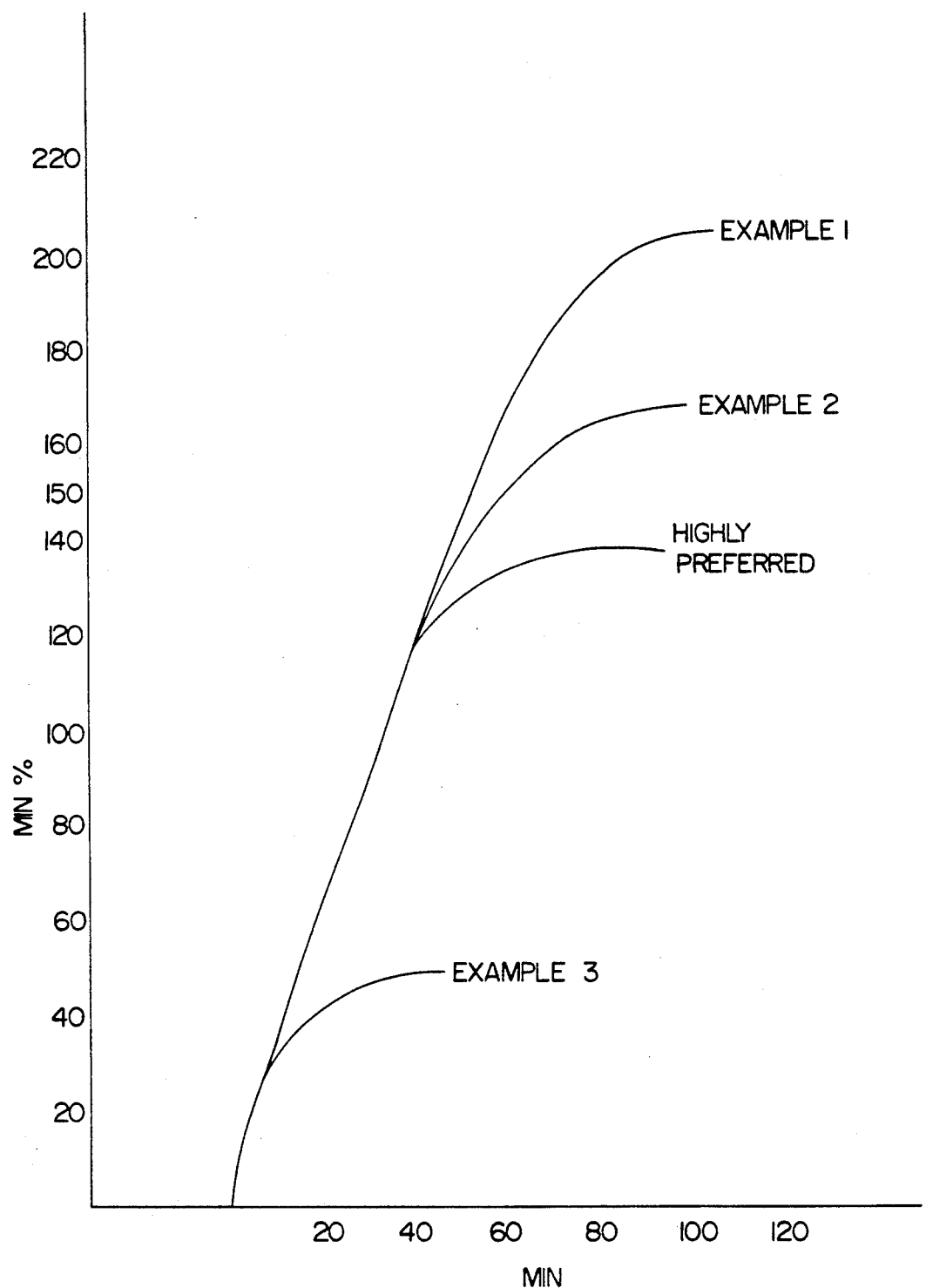
FIG. 6 is a graph showing the decomposition profile of hydrogen peroxide as expressed in terms of cummulative area under the peroxide v. time curve.

The cumulative area under the peroxide % vs. time curve is shown in FIG. 6 for three examples, which will subsequently be described.

Furthermore, in the hydrogen peroxide/oxygen gas system, the residual peroxide content should be with ocularly tolerable levels preferably within less than about 8 hours, preferably less than about 6 hours, more preferably less than about 4 hours, still more preferably less than about 2 hours, most preferably less than about 90 minutes.

Still further the peroxide content should be, at the sample point, at or in excess of a disinfectantly effective concentration (i.e. at or more than 1%) for at least 15 minutes, preferably at least 20 minutes, more preferably at least 30 minutes after decomposition of the approximately 3% hydrogen peroxide solution has begun. When starting with a greater concentration of peroxide, this time period can be shortened provided the % time value for the time the peroxide concentration exceeds 35, preferably 40, in the first 15 minutes of decomposition and exceeds 40, preferably 50, more preferably 55 in the first 20 minutes of decomposition and exceeds 45, preferably 50, more preferably 60, most preferably 80, in the first 30 minutes of decomposition.

In the embodiment of the buoyancy mediated control system as described above, similar considerations apply with appropriate concern for whether the reactant solution is more or less dense than the reaction product solution.

The carrier or substrate for the catalyst can be any material that is resistant to the chemical activity of hydrogen peroxide, the catalyst being used, and oxygen gas. Most preferable for the substrate is a synthetic plastic. Of these, the material of choice is a polycarbonate, especially polycarbonate mixed with acrylate butadiene styrene.

The substrate can be prepared in its desired size and shape by well known techniques, including: extrusion, molding, cutting, chipping, milling, lathing and/or grinding, and coated with catalyst by spraying, dipping, fluidized bed techniques, vapor phase deposition or any other suitable known coating technique so long as the catalyst is not destroyed in the process.

The present invention will be more fully understood with reference to the following examples which illustrate one means of controlling the cumulative exposure of a contact lens to be disinfected by means of a buoyancy mediated control of a catalytic reaction.

THE EXAMPLES

Test procedures were as follows:

Commercial AO Sept cups were filled to the premarked line with about 3.3% hydrogen peroxide (about 9 mls). The system, for peroxide determination, was left open, without the cap or stem inserted. A 50 ul sample was taken and assayed. The catalytic particles used for the invention were placed into the container. Additional 50 ul samples were withdrawn at the specified times from the bottom of the cup (approximately 22 mm from the upper surface of the solution). The typical cup used is shown in FIG. 5.

EXAMPLE 1

6 of 6 mm diameter (pre-coating size) Pt coated balls (polycarbonate mixed with acrylate butadiene styrene, pre-coating density is 1.11 g/ml) were put in AO Sept cups filled with AO Sept solution (3-3.5% $H_2O_2$ with phosphate buffered saline) up to the line, and the concentration of $H_2O_2$ 23-25 mm from the upper surface measured during the interval time. The results are listed on the following table. The (% peroxide·min) vs. min curve is shown in FIG. 6.

EXAMPLE 2

The procedure of Example 1 was repeated except that 4 of 8 mm diameter (pre-coating size) balls (Noryl, pre-coating density is 1.06 g/ml) were employed. The results are listed on the following table. The (% peroxide·min) vs. min curve is shown in FIG. 6.

EXAMPLE 3

The procedure of Example 1 was repeated except that 6 of 4 mm diameter (pre-coating size) balls (polycarbonate, pre-coating density is 1.19 g/ml) were employed. The results are listed on the following table. The (% peroxide·min) vs. min curve is shown in FIG. 5.

The concentration of hydrogen peroxide (%) at the time of interval and after 6 hrs. (ppm).

| Time (min) | Examples 1 | 2 | 3 |
|---|---|---|---|
| 0 | 3.3(%) | 3.3(%) | 3.3(%) |
| 5 | 3.0 | 3.1 | 3.1 |
| 7 | 3.1 | 3.1 | 3.0 |
| 10 | 3.1 | 3.2 | 2.9 |
| 15 | 3.0 | 2.8 | 1.8 |
| 20 | 2.7 | 2.6 | 1.1 |
| 25 | 3.0 | 2.4 | 0.4 |
| 30 | 2.9 | 2.5 | 0.3 |
| 40 | 2.8 | 2.5 | 0.2 |
| 50 | 2.3 | 1.6 | 0.0 |
| 60 | 2.0 | 1.5 | — |
| 75 | 1.7 | 1.2 | — |
| 90 | 0.3 | 0.2 | — |
| 105 | 0.0 | 0.0 | — |
| 120 | — | — | — |
| 6 (hrs) | 60,61 | 4,5 | 2,3 |

-continued

| Time (min) | Examples 1 | 2 | 3 |
|---|---|---|---|
| | (ppm) | (ppm) | (ppm) |

The previous examples exemplify one means of controlling the cumulative exposure rate to at least 20%·min by means of a buoyancy mediated control system. There are other ways of controlling the buoyancy mediated catalytic reaction by flexibly attaching the catalyst to the container in which the hydrogen peroxide decomposition is carried out. This can be done by attaching it to the wall of the container by means of a hinge or a flexible plastic material. This embodiment will be described in respect to the case where a hinge is used, however, it should be understood that other means can be employed to attach the catalyst to the $H_2O_2$ decomposition devices.

HINGED CATALYST DECOMPOSITION MEANS

Figure 10:
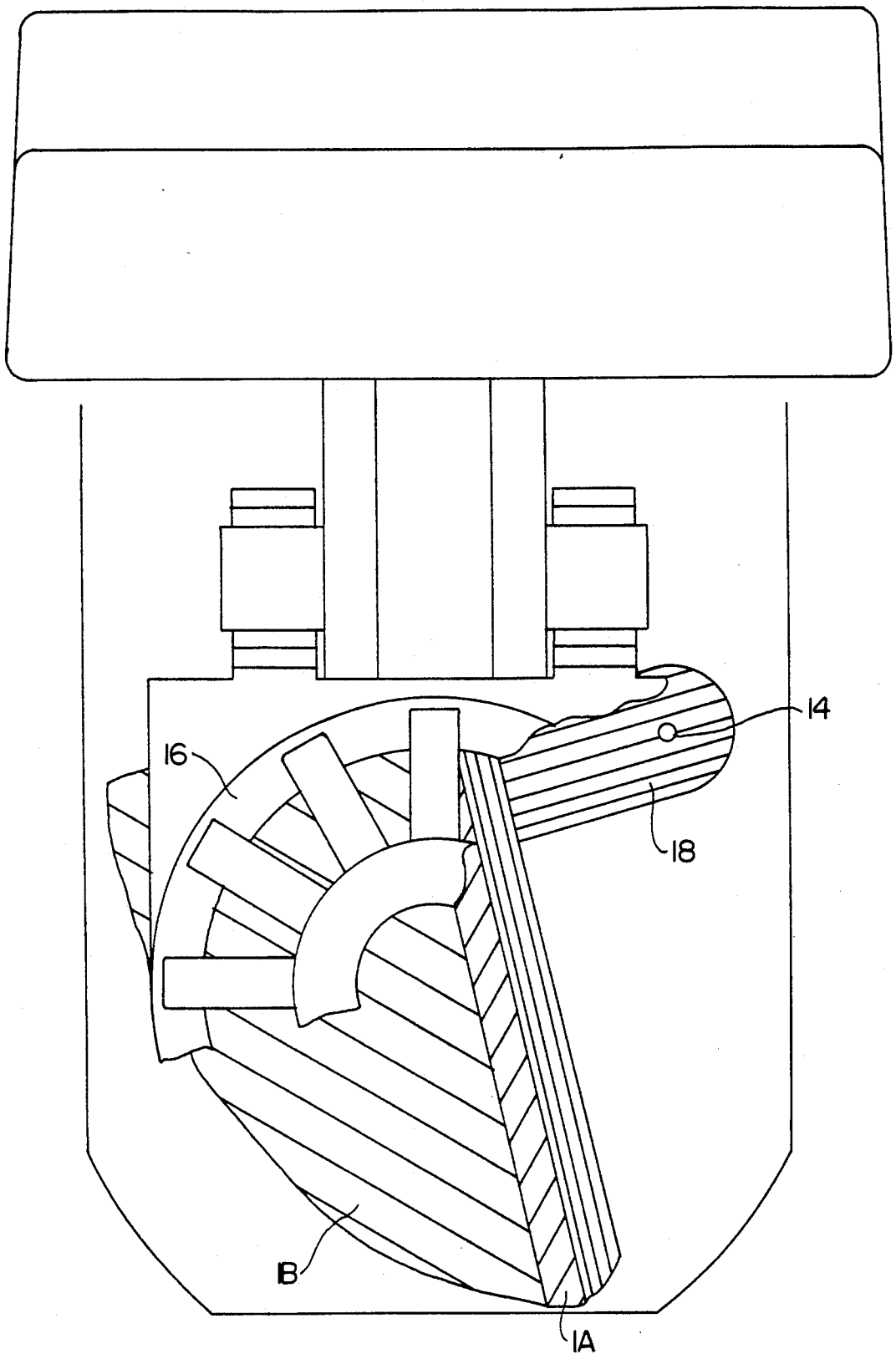
Figure 11:
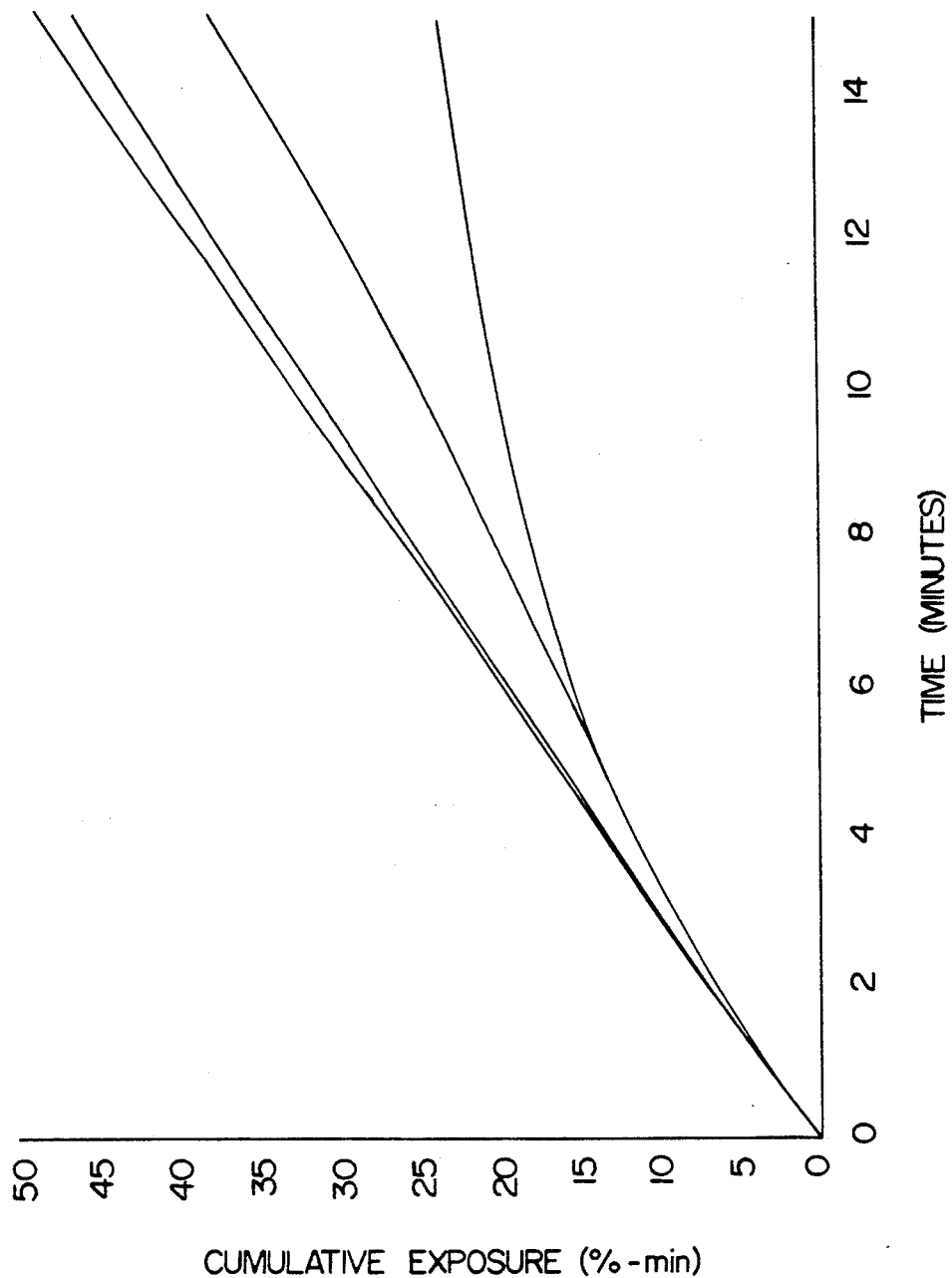
FIGS. 11-15 are graphs plotting the cumulative exposure against time of various hinged catalyst systems with different exposure rates.
Figure 12:
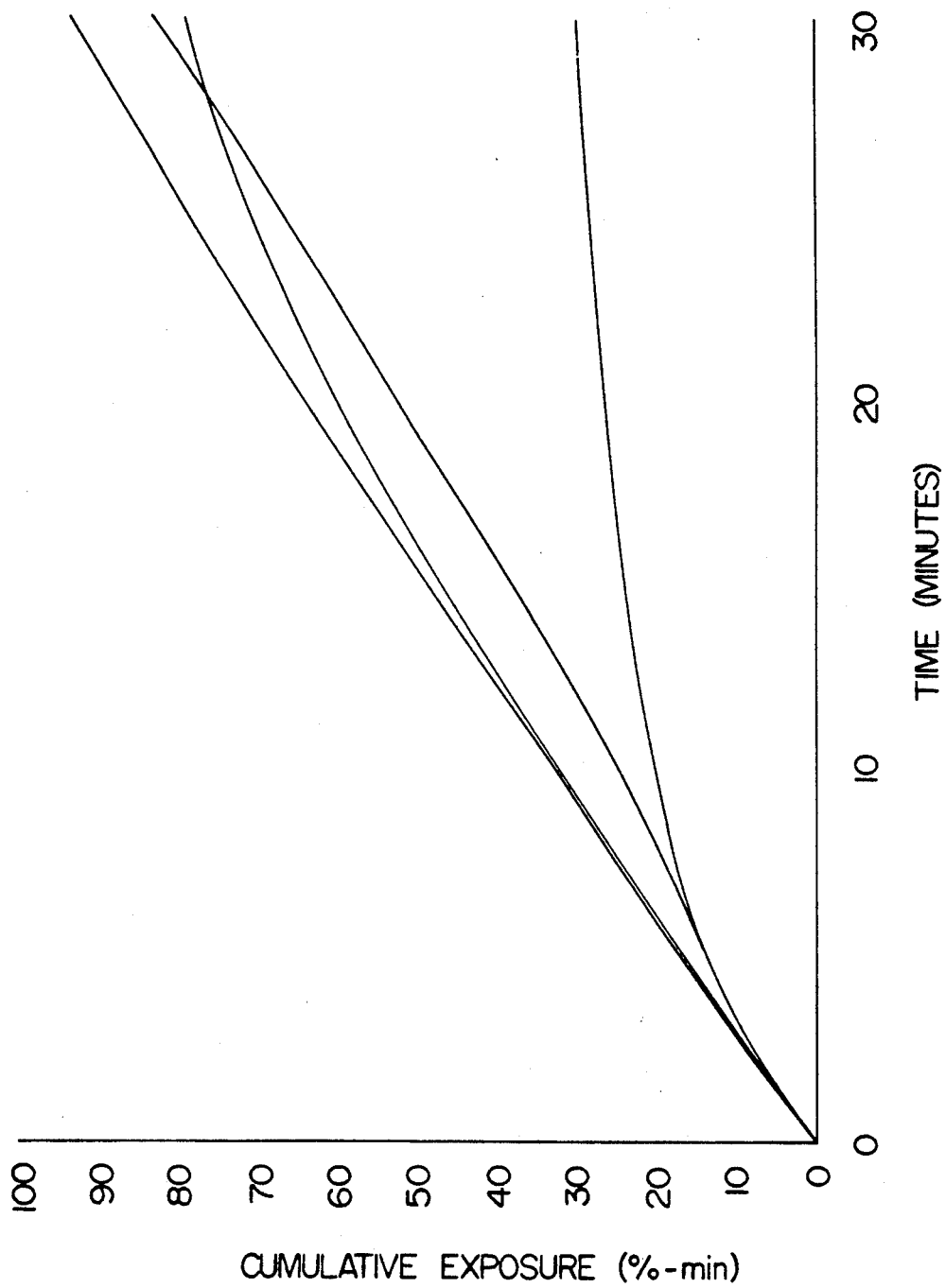
Figure 13:
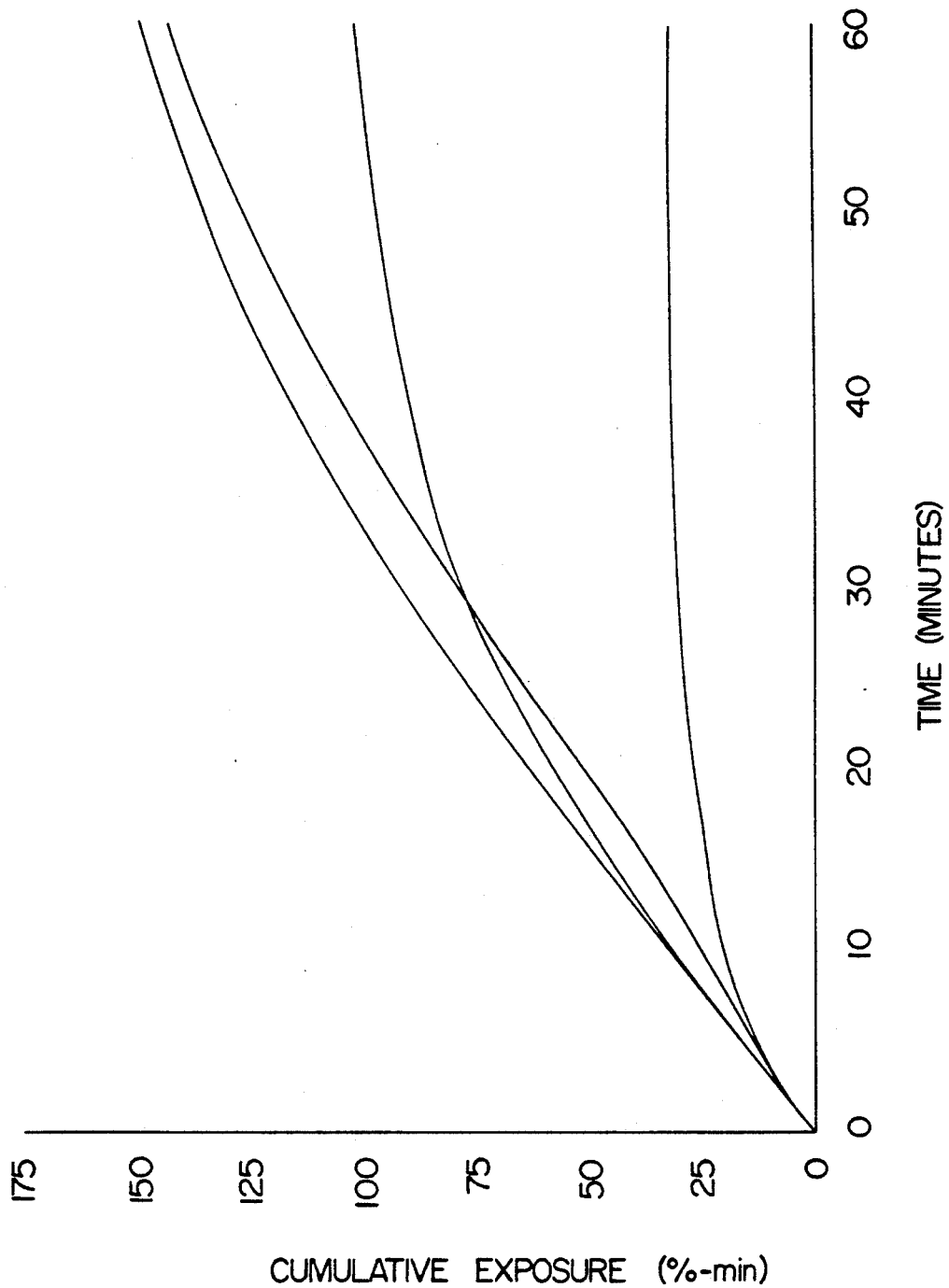
Figure 14:
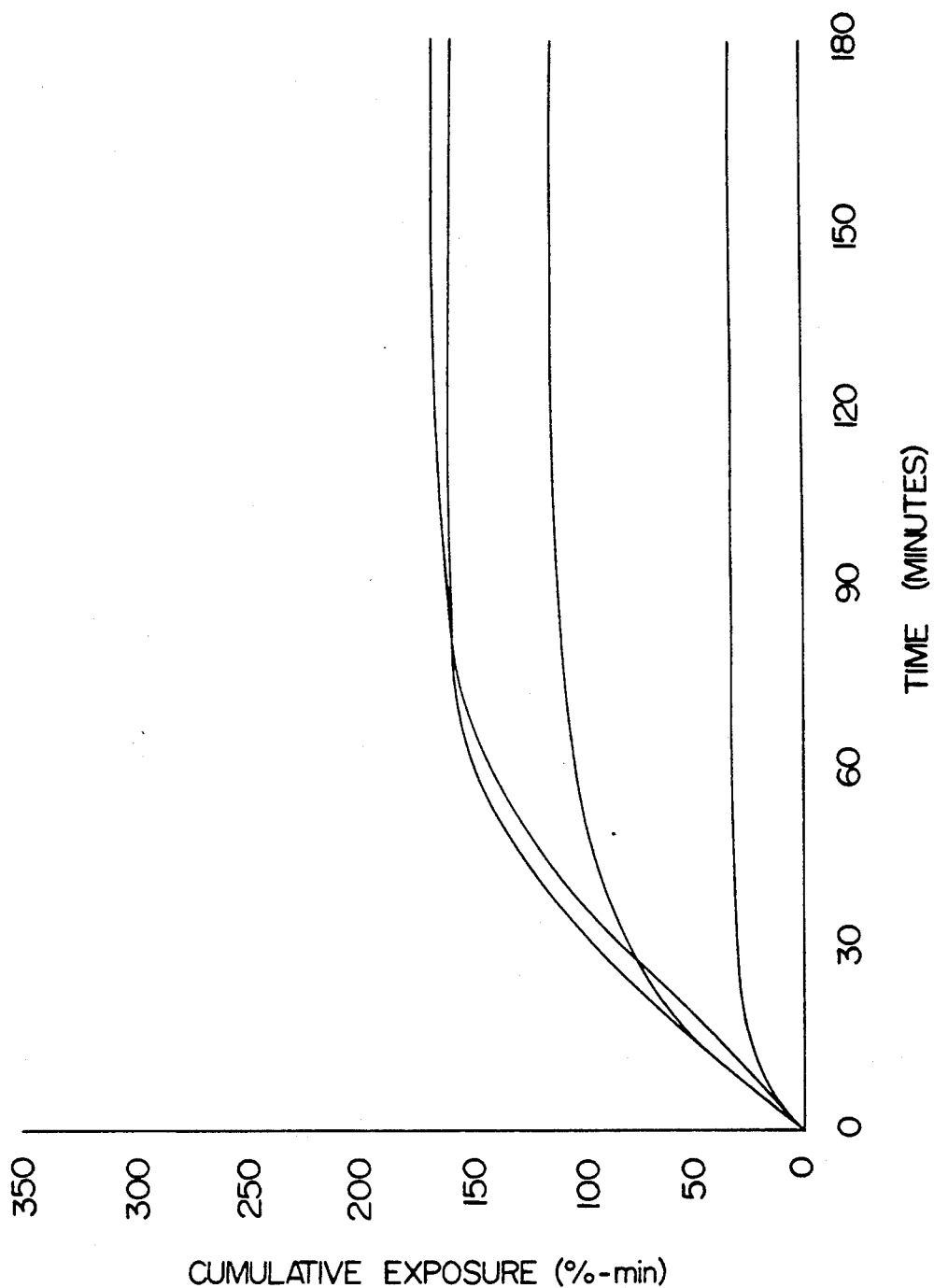
Figure 15:
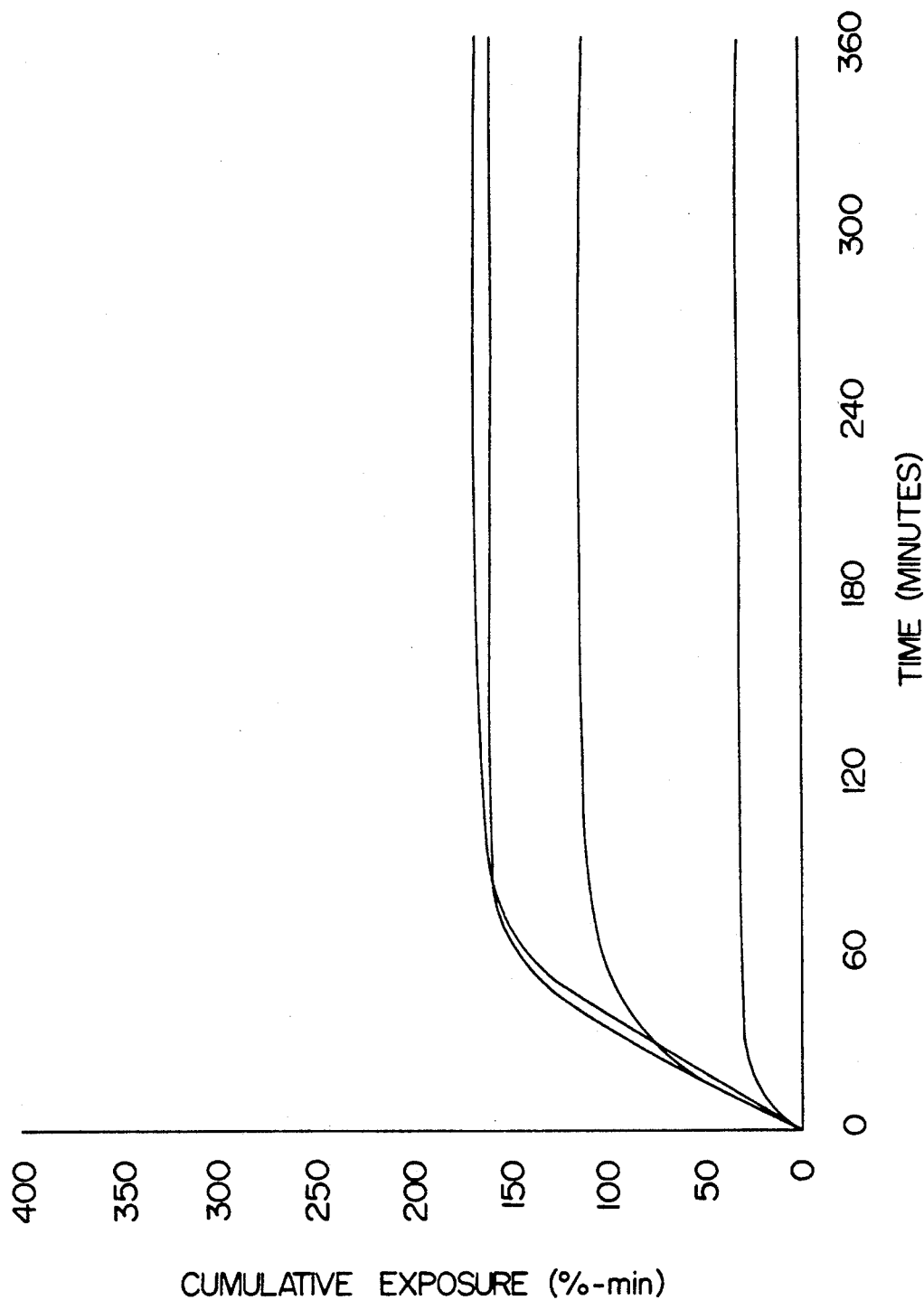

One variation of the buoyancy mediated control of the catalytic reaction resides in attaching the catalyst 1, such as platinum, by means of a hinge 14 to a device in which the catalyst 1 can be lowered and raised in the reaction solution by pivoting around the hinge 14 as shown in FIGS. 7-10 which respectively describe a back view of the catalyst 1 in the up position (FIG. 7), a back view of the catalyst 1 in the down position (FIG. 8), a side view of the catalyst 1 in the up position (FIG. 9) and a side view of the catalyst 1 in the down position (FIG. 10).

According to this embodiment, the average density of the catalytic part 1 must be greater than the density of the solution, otherwise, it will not sink. It must be sufficiently greater such that its sinking will occur over a reasonably short time after the lenses have been adequately disinfected. On the other hand, the density of the catalyst must be sufficiently close to the density of the hydrogen peroxide reaction solution, such that the interreaction with the liberated oxygen is adequate to float the catalyst into its "up position" reasonably quickly when first installed in the solution.

Figure 7:
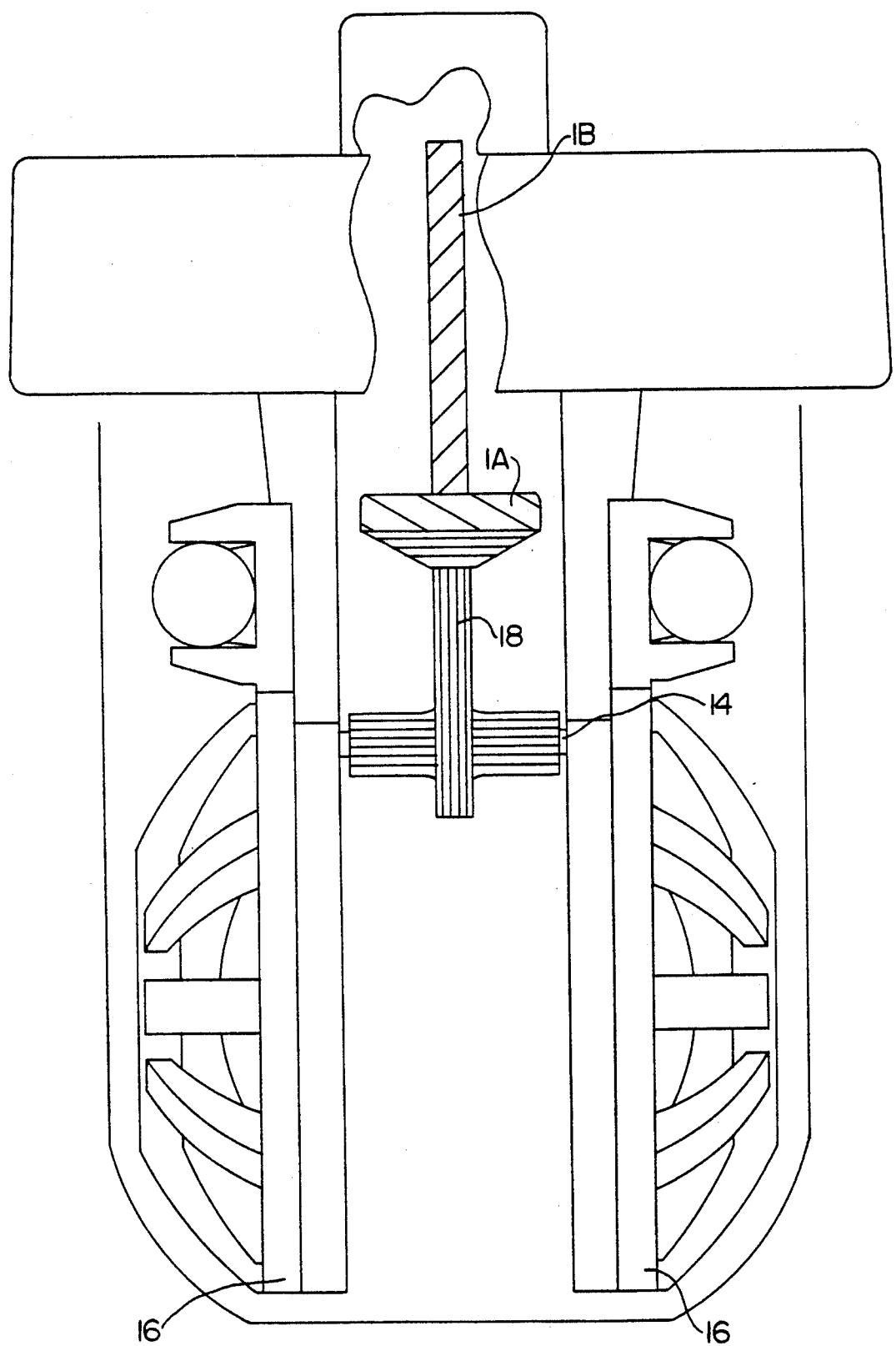
FIGS. 7–10 a hinge catalyst decomposition device which respectively describe a backview of the catalyst in the up position (FIG. 7) a backview of the catalyst in the down position (FIG. 8) a sideview of the catalyst in the up position (FIG. 9) and a sideview of the catalyst in the down position (FIG. 10).
Figure 8:
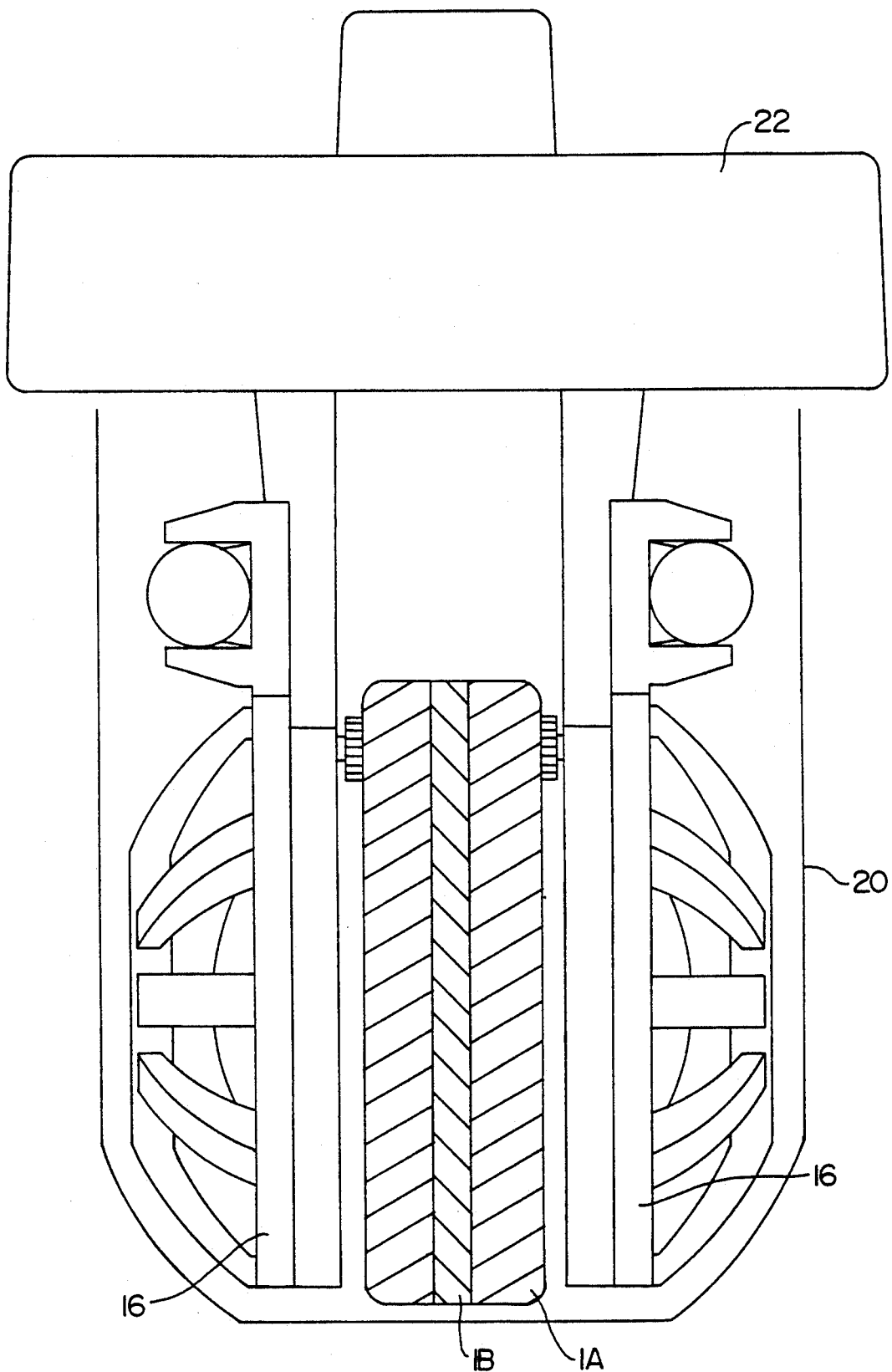
Figure 9:
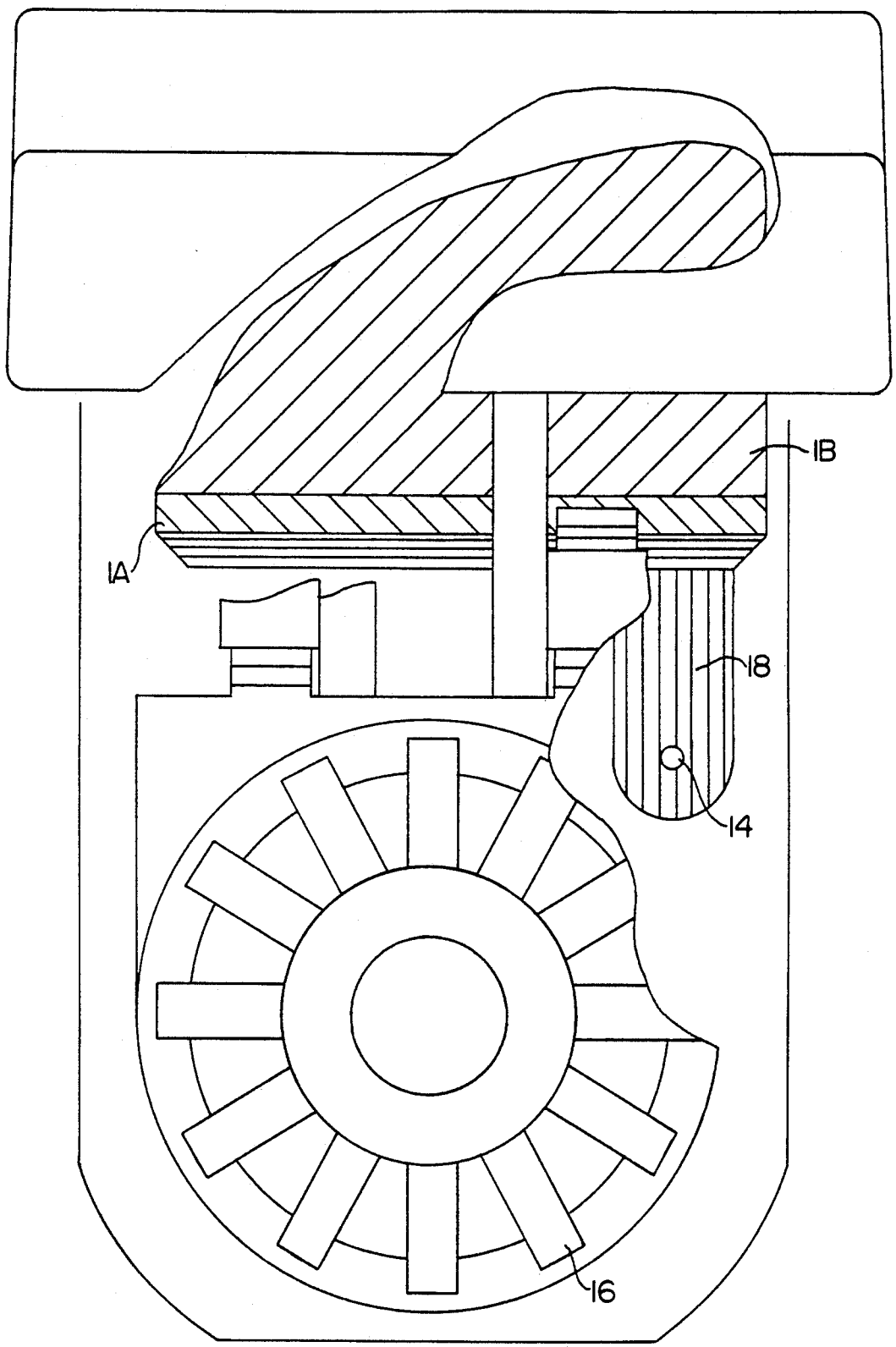

According to the preferred aspects of this hinged device, the catalyst 1 includes a flat plate 1A, which is horizontal in the up position, and a fin portion 1B extending vertically upwardly from the flat plate 1A (see FIG. 7). The flat plate 1A is as wide as permitted by the clearance between lens holders 16. This is shown by FIGS. 7-10 of the drawings. The fin portion 1B attached to the plate 1A is often slanted upward, similar to a ship's keel. The flat plate 1A, and thus the fin portion 1B, are attached to the hinge by an uncoated arm 18. The configuration, as shown in the drawing, generates good front and end performance (about 1% at 60 min.) with respect to the decomposition of the hydrogen peroxide, but typically has a high residual peroxide (75-150 ppm) at 6 hours. The size of the embodiment shown in the drawing was approximately 8 mm wide by 20 mm long up to about 3 mm deep.

A vertical fin has been added to increase the surface area and surface area distribution of the catalyst. The fin is intended to rise above the solution surface when in the up position where it does not speed up the front-end decomposition profile. To raise this fin out of solution, it requires a much greater lifting moment. The larger moment decreases the chance of the catalyst from "hanging up" in the up position. The catalyst typically has a clearance as large as possible, i.e. 1-2 mm between the cup wall during transition from its up to down position. Variation of this device can be used in which 2, 3 or more side fins can be used. Also, vertical fins or side fins perforated to decrease the surface area may be used.

In addition to the above, the mass distribution of the catalyst should be such that the mechanical moment about the hinge axis is less when the catalyst is in the up position. This is accomplished by having the center of the mass of the catalyst just forward of a vertical line through the hinge access, but well above the axis. On the other hand, the horizontal distance of the vertical projection of the center of the mass from the axis is less when the catalyst is in the up position than when it is down. This causes the rotational moment to increase as the catalyst moves from the up to the down position. Therefore, less buoyancy is required in this instance to maintain the catalyst in the up position. This permits it to remain in the up position longer. Also, longer float time yield higher exposures to the disinfectant and improve efficiency. When the catalyst begins to sink, according to this configuration, it will sink quicker due to the increasing rotational moment.

The center of gravity for the catalyst produced can be modified as pointed out above by drilling out holes in the fins, cutting out slots, etc., in an effort to develop a catalyst with good lifting and sinking performance. Further, the catalyst should be near the center of the system. The internal cup diameter should be as narrow as possible in order to pack the solution around the catalyst. The inside diameter of the cups holding the hinge catalyst are about 24 mm-25 mm. The bottom of the cup is rounded for the same reason. The current AO cup is 22 mm i.d.

The amount of surface in contact or intimate contact with the solution is such that the neutralization rate can be reduced during the initial phase by limiting or preventing contact between the solution and the catalyst. This will increase the percent·min. exposure to the disinfectant. The hinge catalyst lifts a segment of the catalyst out of the solution which reduces the total activity. A similar effect can be achieved by reducing the exchange rate of the lower concentration near the catalyst with higher concentration solution away from the catalyst which can be achieved by blocking structures around the catalyst, control of bubble adherence, trapping gas around the catalyst, or by control of the circulation pattern.

The wettability of the catalyst by the solution/bubble adherence is important. That is, the manner in which the liberated oxygen bubbles from the hydrogen peroxide reaction nucleates, expands and releases from the catalyst surface determines how much buoyancy the bubbles impart to the catalyst. Bubbles will become larger on a less wettable surface before they break. Larger bubbles will typically impart more buoyancy per unit of catalyst surface area, but the buoyancy of the catalyst also tends to be less responsive to the concentration of the peroxide. The reverse situation exists for smaller bubbles. The more catalyst surface, the smaller the bubbles will be when they are released.

The wettability of the catalyst surface can be increased by "plasma treatment" by alloying the platinum catalyst with gold or palladium from the sputtered target. In addition, the wettability of the catalyst can be modified by the selection of materials or method of manufacturer's surface finish or by modification of the solution with a wetting agent such as propylene glycol, glycerol, or pluronic L-31. The cumulative exposure of a platinum catalyst in a 3-3.5 percent hydrogen peroxide solution is illustrated in FIGS. 11-15 in which the cumulative exposure of the hinged catalyst systems are plotted against various time intervals varying from up to 15 minutes to up to about 6 hours. In such graphs, there are four lines which are based upon platinum catalyst systems of different cumulative exposure rates, based upon the wettabilities of the catalysts, etc., which fall within the cumulative exposure parameters of the present invention.

STIR BAR SYSTEM

Figure 16:
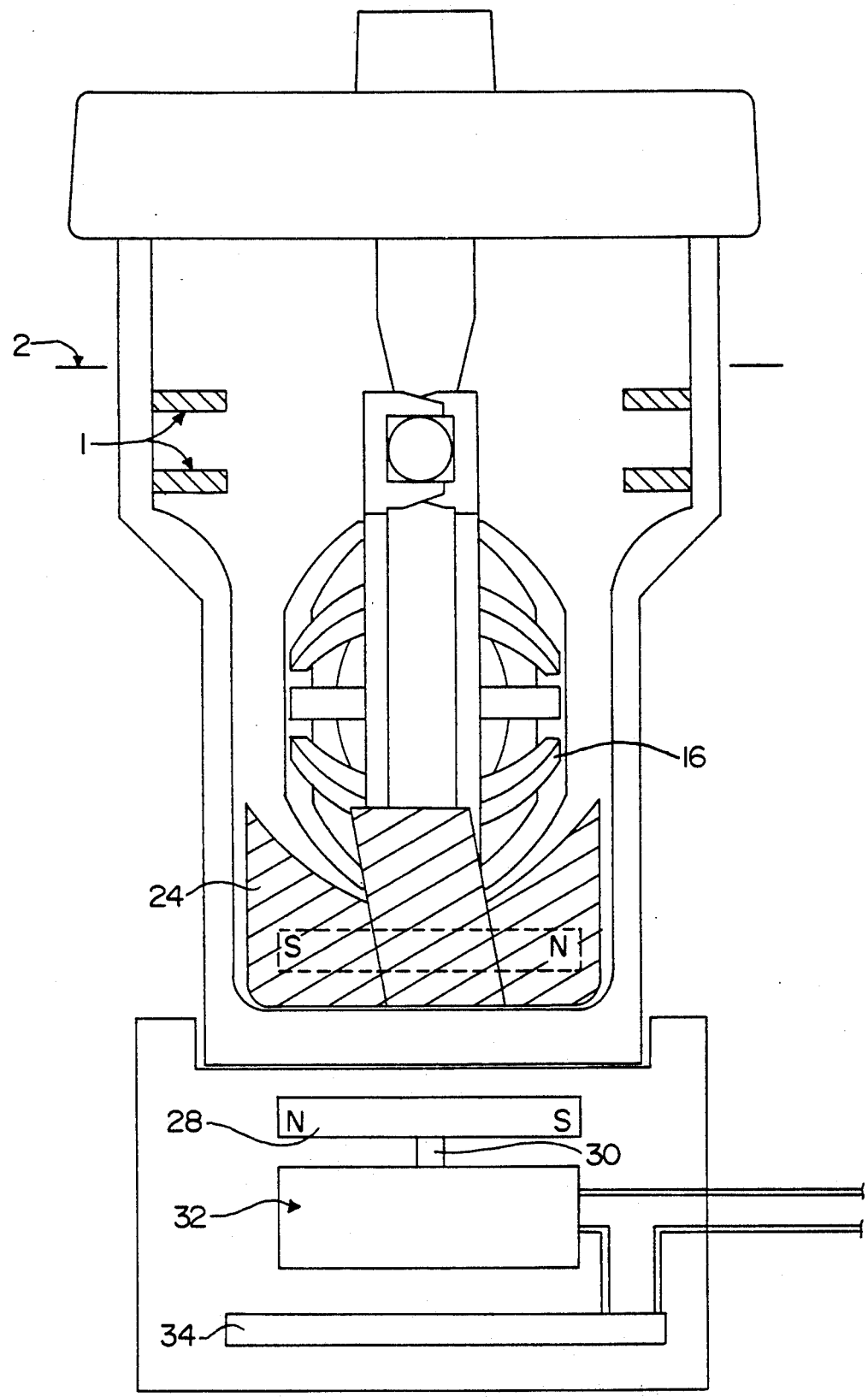
FIG. 16 is a stir bar system whereby contact between the catalyst and the reaction solution is controlled by means of the stirring action of a stir bar.

There is another way of controlling the decomposition rate of the hydrogen peroxide solution by means of the stir bar system shown in FIG. 16. This is by means of fixing the catalyst 1 to the container 20 near the top of the container and just below the level 2 to which the solution is to be filled so that it is in contact with the hydrogen peroxide solution. Located at the bottom of the hydrogen peroxide decomposition device is a stirring means such as a stir bar or impeller 24 for agitating the system such that fresh $H_2O_2$ is continually brought in contact with the catalyst 1. This is similar to the buoyancy mediated catalyst control system in that the contact between the catalyst 1 and the reaction solution is controlled by means of the stirring action of the stir bar or impeller 24 so that the reaction product solution is removed from the vicinity of the catalyst 1 and hydrogen peroxide (the reaction solution) is continuously supplied to said catalyst as a result of the stirring action of the stir bar or impeller 24. The stir bar or impeller 24 can be driven by any suitable means, but, in the preferred embodiment shown in FIG. 16, the impeller 24 is driven by a magnetic drive system. Such system includes a first magnet 26 embedded in the impeller 24 and a second magnet 28 mounted to a shaft 30 extending from a motor 32. The motor 32 is adapted to rotate the second magnet 38, which, due to the polarity of the two magnets, will cause rotation of the first magnet 26, and thus of the impeller 24. It is also contemplated that a timer/controller 34 be operatively connected to the motor 32 to provide desired control of the activation, deactivation and rotational speed of the motor. The motor and timer/controller can be operated by any suitable power supply, but it is preferred that it be a DC power supply. This stirring, of course, is correlated such that the cumulative exposure is controlled so as to be at least 20% peroxide·min over a period of no greater than 12 hours. Thus, according to this procedure the catalyst may be first immersed in the $H_2O_2$ solution without stirring and the stirring commenced after the $H_2O_2$ is decomposed in the vicinity of the catalyst and the reaction product solution thus-formed is subsequently removed and fresh $H_2O_2$ supplied by the subsequent stirring action.

In all of these systems described, a conventional $H_2O_2$ decomposing device commonly used to disinfect contact lenses may be used such as described in parent application Ser. No. 07/458,123, but which has been modified to contain the stir bar features, hinge device 14 and other decomposition means, etc., as described above. According to said parent application, the device used to effect peroxide disinfection on a non-continuous basis comprises a vessel with a vial or lens cup (such as 20 in FIGS. 7-10) having an opening at one end thereof, a cap or cover (such as 22 in FIGS. 7-10) for sealing said vial from the environment, a release valve in said cap or vial walls or a cap-vial junction to release gas pressure buildup, and a means for restricting the position of the contact lenses undergoing disinfection at a position distal to the opening of said vial. This embodiment further may optionally contain a sleeve or web which allows movement of the catalyst particles therethrough in the vertical direction between the opening end portion of the vial distal thereto.

OTHER CONSIDERATIONS

According to the general limitations of the present invention, the cumulative (percent peroxide) (min) exposure of the hydrogen peroxide from the point said contact occurs over a period of not greater than 12 hours is at least 20% peroxide·min. However, in certain preferred instances, the period of exposure can be lessened to periods ranging from periods of no greater than 1.5 hours or periods ranging from periods no greater than 2 hours, 4 hours, 6 hours, 8 hours or no greater than 10 hours, depending upon the disinfectant objectives to be achieved, the degree of contamination of the device, etc. At the end of any of these time periods, the resulting solution should have a residual hydrogen peroxide content which is no greater than an ocularly acceptable amount, such that the contact lens can be inserted into the eye. Preferably, the hydrogen peroxide content should be no greater than about 200 ppm, more preferably no greater than 100 ppm and in certain instances no greater than 75 ppm, still more preferably no greater than 60 ppm and ideally no greater than 30 ppm.

The hydrogen peroxide content at time zero should range from 0.5 to about 6%, preferably 1 to about 4%, more preferably about 2.5 to about 3.5% and most preferably between about 3.0 to 3.5%.

Further, as previously pointed out, the initial oxygen generation rate in conventional AO Sept system ranges from about 40 to 90 ml/min. These rates yield less than 10% minutes when correlated to the cumulative exposure. An initial rate of less than about 20 ml/min. is required to yield 20% · min. according to the present invention. This is the cumulative exposure. The cumulative exposure over the full cycle until the time when the hydrogen peroxide reaches an ocularly acceptable level is referred to as the total exposure for the hydrogen peroxide system.

According to the present invention, the cumulative exposure of the material to be disinfected to the hydrogen peroxide between time zero and 15 minutes should be no more than 95% of the total exposure. More preferably, the cumulative exposure to hydrogen peroxide between the time zero and 15 minutes should be preferably no more than 50% of the total exposure.

Yet in another preferred limitation, the cumulative exposure to the hydrogen peroxide between time zero and 20 minutes later should be no more than 97% of the total exposure and preferably no more than 65% of the total exposure.

A cumulative exposure to hydrogen peroxide between time zero and 30 minutes later should be no more than 99% of the total exposure and preferably no more than 85% of the total exposure. The cumulative exposure of the present invention should preferably be at least 20% peroxide·min. over a time ranging from about 15 to 30 minutes at the minimum in respect to the total exposure, preferably higher than 30 minutes, more preferably at least 60 minutes and most preferably at least about 1.5 hours at the minimum to a period of no greater than 12 hours.

Other than those specific embodiments disclosed in the present application, there are many other specific variations which will be apparent to those skilled in the art, once Applicants' essential inventive concept is grasped.

What is claimed is:

1. A method of disinfecting a hydrogen peroxide stable material comprising contacting said material with a hydrogen peroxide containing solution and a hydrogen peroxide decomposition means which permits said material to have a cumulative (% peroxide)(min) exposure from the time said decomposition means contacts said peroxide containing solution, time zero, over a period of no greater than 12 hours of at least 20% peroxide·min., said hydrogen peroxide containing solution having a hydrogen peroxide content at time zero of from about 0.5 to about 6%, and wherein said decomposition means is a member selected from the group consisting of (a) a catalyst fixed to a position which is at the bottom of said solution, said catalyst being prepoisoned to partially deactivate the active sites of the catalyst to slow down the decomposition rate of the hydrogen peroxide solution, (b) a catalyst flexibly attached to a portion of a hydrogen peroxide decomposing device in which the disinfecting is carried out so as to move out of and into said solution during said decomposition process, (c) a catalyst enclosed within a container located within a hydrogen peroxide decomposing device in which said disinfecting is carried out, said container having one or more orifices therethrough so as to restrict the flow rate of oxygen from inside the container to the exterior of the container, (d) a catalyst free floating in said solution with a density to drive it into unreacted solution areas and sufficiently light to be driven away from said unreacted solution areas by buoyant forces resulting from oxygen bubbles adherent thereto, and (e) a catalyst located in a position at the top of a hydrogen peroxide decomposing device in which said disinfecting is carried out and which is in contact with the hydrogen peroxide solution, whereby the decomposition of the hydrogen peroxide is controlled by a stirring means located at the bottom of said hydrogen peroxide decomposition device which stirring means functions by agitating the hydrogen peroxide liquid solution such as to remove the reaction product formed from the vicinity of the catalyst and bring the unreacted hydrogen peroxide in fresh contact with the catalyst.

2. The method of claim 1 wherein said material is a polymeric plastic.

3. The method of claim 1 wherein said material is an ophthalmic device.

4. The method of claim 1 wherein said material is a contact lens.

5. The method of claim 1 wherein said period is no greater than about 10 hours.

6. The method of claim 1 wherein said period is no greater than about 8 hours.

7. The method of claim 1 wherein said period is no greater than about 6 hours.

8. The method of claim 1 wherein said period is no greater than about 4 hours.

9. The method of claim 1 wherein said period is no greater than about 2 hours.

10. The method of claim 1 wherein said period is no greater than about 1.5 hours.

11. The method of claim 1 wherein said material is ocularly insertable and the resulting solution has a residual hydrogen peroxide content at the conclusion of said period which is no greater than an ocularly acceptable amount.

12. The method of claim 1 wherein at the conclusion of said period, the resulting solution has a residual hydrogen peroxide content of no greater than 400 ppm.

13. The method of claim 12 wherein the residual hydrogen peroxide content is no greater than about 200 ppm.

14. The method of claim 12 wherein the residual hydrogen peroxide content is no greater than about 100 ppm.

15. The method of claim 12 wherein the residual hydrogen peroxide content is no greater than about 75 ppm.

16. The method of claim 12 wherein the residual hydrogen peroxide content is no greater than about 60 ppm.

17. The method of claim 12 wherein the residual hydrogen peroxide content is no greater than about 30 ppm.

18. The method of claim 1 wherein said hydrogen peroxide containing solution has a hydrogen peroxide content at time zero of from about 0.5 to about 6%.

19. The method of claim 18 wherein said hydrogen peroxide content at time zero is from about 1 to about 4%.

20. The method of claim 18 wherein said hydrogen peroxide content at time zero is from about 2.5 to about 3.5%.

21. The method of claim 18 wherein said hydrogen peroxide content at time zero is from about 3.0 to about 3.5%.

22. The method of claim 1 wherein said material has a cumulative (% peroxide)(min) exposure between time zero and 15 minutes later of no more than 95% of the total exposure.

23. The method of claim 22 wherein said material has a cumulative (% peroxide)(min) exposure between time zero and 15 minutes later of no more than 50% of the total exposure.

24. The method of claim 22 wherein said material has a cumulative (% peroxide)(min) exposure between time zero and 20 minutes later of no more than 65% of the total exposure.

25. The method of claim 22 wherein said material has a cumulative (% peroxide)(min) exposure between time zero and 30 minutes later of no more than 85% of the total exposure.

26. The method of claim 1 wherein said material has a cumulative (% peroxide)(min) exposure between time zero and 20 minutes later of no more than 97% of the total exposure.

27. The method of claim 1 wherein said material has a cumulative (% peroxide)(min) exposure between time zero and 30 minutes later of no more than 99% of the total exposure.

28. The method of claim 1 wherein said decomposition means is a catalyst.

29. The method of claim 1 wherein said decomposition means is reactive with hydrogen peroxide.

30. The method according to claim 1 wherein the hydrogen decomposition means comprises buoyant, free floating particles of a hydrogen peroxide decomposition agent, alone or coated on or contained within an inert, hydrogen-peroxide-decomposition agent carrier.

31. The method according to claim 1 wherein the hydrogen peroxide decomposition means comprises a shaped catalyst, alone or in a carrier therefor, movably attached to a portion of a container in which said hydrogen peroxide decomposition is carried out.

32. The method of claim 31 wherein said shaped catalyst is movably attached to a wall of said container.

33. The method of claim 31 wherein said container comprises at least one holding portion to hold the material to be disinfected, said catalyst being movably attached to at least one of said holding portions.

34. A method of decomposing a hydrogen peroxide solution comprising contacting said solution with a hydrogen peroxide decomposition means which permits a material placed in said solution to have a cumulative (% peroxide)(min) exposure to hydrogen peroxide from the point said contacting occurs over a period of not greater than 12 hours of at least 20% peroxide·min.

* * * * *